United States Patent
Takahashi

[11] Patent Number: 6,166,261
[45] Date of Patent: Dec. 26, 2000

[54] OXIDATION CATALYTIC SYSTEM AND PROCESS FOR PRODUCING KETOISOPHORONE USING THE SAME

[75] Inventor: Ikuo Takahashi, Kobe, Japan

[73] Assignee: Daicel Chemical Industries, Ltd., Osaka, Japan

[21] Appl. No.: 09/316,141

[22] Filed: May 21, 1999

[30] Foreign Application Priority Data

Jun. 1, 1998 [JP] Japan ................... 10-151644

[51] Int. Cl.$^7$ ................... C07C 45/27
[52] U.S. Cl. ................ 568/344; 568/338; 568/357; 568/377
[58] Field of Search .............. 568/344, 338, 568/357, 377

[56] References Cited

U.S. PATENT DOCUMENTS

| | | | |
|---|---|---|---|
| 3,354,220 | 11/1967 | Brackman et al. | 260/586 |
| 5,874,632 | 2/1999 | Hahn et al. | 568/344 |

FOREIGN PATENT DOCUMENTS

| | | |
|---|---|---|
| 669244 | 3/1966 | Belgium . |
| 2303785 | 10/1976 | France . |
| 49-81347 | 8/1974 | Japan . |
| 50-93947 | 7/1975 | Japan . |
| 51-25316 | 11/1976 | Japan . |
| 55-30696B2 | 8/1980 | Japan . |
| 61-191645 | 8/1986 | Japan . |
| 63-122644 | 5/1988 | Japan . |
| 1-090150 | 4/1989 | Japan . |
| 1-175955 | 7/1989 | Japan . |
| 10-053553 | 2/1998 | Japan . |

OTHER PUBLICATIONS

M. Constantini et al., *Journal of Molecular Catalysis*, vol. 7, pp. 89–97, (1980).
The Chemical Society of Japan, *Chemistry Letters*, No. 7, pp. 1081–1082, (1983).

*Primary Examiner*—Sreeni Padmanabhan
*Attorney, Agent, or Firm*—Birch, Stewart Kolasch & Birch, LLP

[57] ABSTRACT

In the presence of a catalytic system comprising a cyclic base and a complex of a transition metal with an N,N'-disalicylidenediamine, ketoisophorone or a derivative thereof is produced by oxidizing β-isophorone or a derivative thereof with molecular oxygen with controlling the water content of a reaction system to 1% by weight or less at the initial stage of the reaction. Moreover, the above catalytic system further comprises a basic nitrogen-containing compound. The complex may be an N,N'-disalicylidene $C_{2-5}$ alkylenediamine complex with manganese, iron, cobalt, copper, or vanadium. The cyclic base may be an alicyclic or aromtaic compound having at least two nitrogen atoms. As the basic nitrogen-containing compound, a Schiff base such as an imino compound and an anil compound can be used. The proportion of the nitrogen-containing compound to the complex is about 0.1/1 to 20/1 (molar ratio). With the above oxydation catalytic system, there can be obtained ketoisophorone and derivatives thereof with high efficiency.

19 Claims, No Drawings

OXIDATION CATALYTIC SYSTEM AND PROCESS FOR PRODUCING KETOISOPHORONE USING THE SAME

FIELD OF THE INVENTION

The present invention relates to an oxidation catalytic system and a process for producing ketoisophorone using the same, particularly to an oxidation catalytic system useful in producing ketoisophorone by oxidizing β-isophorone with molecular oxygen and a process for producing ketoisophorone using the same.

BACKGROUND OF THE INVENTION

Ketoisophorone (4-oxoisophorone) is an intermediate product useful as a starting material of medicines, perfumes, condiments, and a component for polymers.

As a process for producing ketoisophorone from isophorone, Japanese Patent Publication No. 30696/1980 (JP-B-55-30696) discloses a method for producing 4-oxoisohporone by oxidizing α-ishophorone with oxygen in the presence of a phosphomolybdic acid or a silicomolybdic acid. Japanese Patent Application Laid-Open No.191645/1986 (JP-A-61-191645) discloses a process for producing 4-oxoisophorone by oxidizing α-isophorone with oxygen in the coexistence of a phosphomolybdic acid or a silicomolybdic acid and an alkaline metal compound or an aromatic amine. Japanese Patent Application Laid-Open No. 93947/1975 (JP-A-50-93947) discloses a method for producing 4-oxoisophorone by oxidizing α-isophorone in the gas phase in the presence of a vanadium catalyst. Japanese Patent Application Laid-Open No. 81347/1974 (JP-A-49-81347) discloses a method for producing 4-oxoisophorone by oxidizing α-isophorone with an alkaline metal chromic acid salt or a dichromate or a chromium trioxide. In Chem. Lett. (1983), (7), 1081, there is disclosed a method for producing 4-oxoisophorone by oxidizing α-isophorone using t-butylhydroperoxide in the presence of a palladium catalyst. However, in these methods, the selectivity of ketoisophorone is reduced, therefore separation of the formed by-product(s) or a metal catalyst and purification of the object compound are complicated. Moreover, these methods involve using a heavy metal compound requiring special treatment, such as chromium, or a peroxide needed to be handled with care, which results in a decrease in working efficiency.

Moreover, as a method for producing ketoisophorone from β-isophorone, Japanese Patent Application Laid-Open No. 125316 (JP-A-51-125316) discloses a method for producing an ethylenically unsaturated dicarboxylic acid by oxidizing β-ethylenically unsaturated ketone with molecular oxygen or a molecular oxygen-containing gas in the presence of an inorganic base or an organic base and a cobalt or manganese chelate. In this method, however, the yield of ketoisophorone is low due to the use of a straight-chain secondary or tertiary amine such as triethylamine as the organic base.

Further, Japanese Patent Application Laid-Open No. 53553/1998 (JP-A-10-53553) discloses a method for producing ketoisophorone by oxidizing β-isophorone with molecular oxygen in the presence of a manganese complex salt, an organic base, a specific substance having a catalytic action, and water. In this method, there is disclosed an addition of, e.g., an organic acid having a pKa value of 2 to 7 or a corresponding aldehyde, a $C_{1-4}$ aliphatic alcohol or phenol, a compound formable in enolic form, or lithium sulfate as the specific substance having a catalytic action.

According to this method, however, the specific substances decrease, depending on the species of the bases, the conversion or selectivity of the substrate considerably or cause the isomerization of β-isophorone to α-isophorone. Particularly, a higher concentration of β-isophorone in the reaction system causes a considerable decrease in the yield of ketoisophorone. For example, when the concentration of β-isophorone is 20% by weight or more, the conversion and/or the selectivity is decreased to a large extent. Therefore, relatively large amounts of the manganese complex salt and the organic base are required for an improved conversion. Further, a lower concentration of oxygen remarkably decreases the reaction rate and consequently the conversion.

SUMMARY OF THE INVENTION

Thus, an object of the invention is to provide an oxidation catalytic system for producing ketoisophorone from β-isophorone as a substrate with high conversion and selectivity, and a process for producing ketoisophorone using the same.

Another object of the invention is to provide an oxidation catalytic system which achieves an efficient oxidation reaction even with the use of air as a source of molecular oxygen and without the addition of an organic acid having a pKa value of 2 to 7 or a corresponding aldehyde, a $C_{1-4}$ aliphatic alcohol or phenol, a compound capable of forming the enolic foam, or lithium sulfate, and a process for producing ketoisophorone using the same by employing a cyclic base and a complex of a transition metal with an N,N'-disalicylidenediamine.

Yet another object of the present invention is to provide an oxidation catalytic system capable of significantly improving the conversion of a substrate and the selectivity of the object compound with the use of a cyclic base and a catalytic amount of a basic nitrogen-containing compound in combination, and a process for producing ketoisophorone using the same.

The inventors of the present invention did intensive investigations to achieve the above objects and found that, β-isophorone can be oxidized to ketoisophorone with high conversion and selectivity by controlling the water content at the initial stage of the reaction and using a catalytic system comprising combinatorially a complex of a transition metal with an N,N'-disalicylidenediamine and a cyclic base, and that the conversion and the selectivity can be remarkably improved by using combinatorially the catalytic system with a basic nitrogen-containing compound. The present invention is accomplished based on the above findings.

Thus, the oxidation catalytic system of the present invention comprises at least a cyclic base and a complex of a transition metal with an N,N'-disalicylidenediamine. According to the present invention, ketoisophorone or a derivative thereof is produced by oxidizing β-isophorone or its derivative with molecular oxygen in the presence of a catalytic system comprising a cyclic base and a complex of a transition metal with an N,N'-disalicylidenediamine with controlling the water content in a reaction system to 1% by weight or less at the initial stage of the reaction.

Further, the oxidation catalytic system of the present invention includes an catalytic system comprising a complex of a transition metal with an N,N'-disalicylidenediamine, a cyclic base, and a basic nitrogen-contalning compound. The complex may be an N,N'-disalicylidene $C_{2-5}$ alkylenediamine complex with manganese, iron, cobalt, copper, or vanadium. The cyclic base may be an alicyclic or aromatic compound having at least one nitrogen atom as a hetero atom. The cyclic base may be an alicyclic or aromatic compound having at least two nitrogen atoms. As the basic nitrogen-containing compound, use can be made of Schiff bases such as imino compounds and anil compounds. The amount of the nitrogen-containing compound relative to the complex is the former/the latter=about 0.1/1 to 20/1 (molar ratio). The present invention further includes a process for oxidizing β-isophorone or its derivative with molecular oxygen using the above oxidation catalytic system to produce a corresponding ketoisophorone and its derivative.

In the specification, the term "N,N'-salicylidenediamine" is taken to mean that an N,N'-salicylidenediamine may have a structure in which a salicylidene group is bound to a nitrogen atom of each amino moiety of an aliphatic, alicyclic, or aromatic diamine.

Further, in the present specification, the term "a complex" is used regardless of whether the complex is a complex salt or a chelate with a ligand coordinated therein.

DETAILED DESCRIPTION OF THE INVENTION

According to the present invention, ketoisophorone or a derivative thereof is produced by oxidizing β-isophorone or its derivative with molecular oxygen in the presence of an oxidation catalytic system containing a cyclic base and a complex of a transition metal with an N,N'-disalicylidenediamine with controlling the water content in a reaction system to 1% by weight or less at the first or initial stage of the reaction (e.g., at the beginning of the reaction).

The above oxidation catalytic system comprises a cyclic base and a complex of a transition metal with an N,N'-disalicylidenediamine, and is useful for producing ketoisophorone or a derivative thereof by oxidizing β-isophorone or its derivative with molecular oxygen. By using the above oxidation catalytic system, ketoisophorone or a derivative thereof can be produced efficiently without adding an organic acid having a pKa value of 2 to 7 or a corresponding aldehyde, a $C_{1-4}$ aliphatic alcohol or a phenol, a compound capable of forming the enolic form, or lithium sulfate to a catalytic system.

[Complex]

The complex comprises a transition metal and a ligand, and is used as a catalyst in an oxidation reaction of from β-isophorone or its derivative to form ketoisophorone or its derivative. The complex may be either crystalline or non-crystalline (amorphous).

The species or the valence of a transition metal for the complex is not particularly restricted provided that the transition metal has oxidizability in the above oxidative reaction, and at least one transition metal selected from the elements of the Groups 3 to 12 of the Periodic Table of the Elements can be used. Moreover, the transition metal may be of any valence and selected from divalent to octavalent, and usually of divalent, trivalent, or tetravalent. Examples of the preferred transition metal are the Group 5 elements (e.g., vanadium V, niobium Nb), the Group 6 elements (e.g., chromium Cr), the Group 7 elements (e.g., manganese Mn, rhenium Re), the Group 8 elements (e.g., iron Fe, ruthenium Ru), the Group 9 elements (e.g., cobalt Co, Rhodium Rh), the Group 10 elements (e.g., nickel Ni, palladium Pd), and the Group 11 elements (e.g., copper Cu). The preferred metal is, for example, V, Mn, Fe, Co, Cu and the like, and Mn is particularly preferred. These transition metals can be used either singly or in combination.

The transition metal forms a complex shown by the following formula (1) together with a ligand N,N'-disalicylidenediamine.

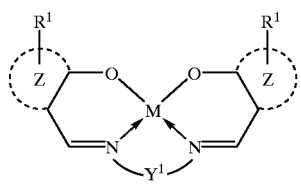

wherein M stands for the above transition metal; $R^1$ and $R^2$ are the same or different and each represents hydrogen atom, a halogen atom, an alkyl group, a hydroxyl group, an alkoxy group, or a hydroxymethyl group; $Y^1$ represents an alkylene group, a cycloalkylene group, or an arylene group; and the ring Z represents an aromatic ring.

As a diamine corresponding to the above $Y^1$, there may be exemplified aliphatic diamines such as a straight- or branched chain $C_{2-10}$ alkylenediamines and a $C_{2-10}$ alkylenediamine containing an imino group (NH group); alicyclic diamines such as a diaminocyclohexane; and $C_{6-12}$ aromatic diamines such as a diaminobenzene, a diaminonaphthalene, a biphenyldiamine and derivatives thereof.

Examples of the preferred N,N'-disalicylidenediamine are N,N'-disalicylidene $C_{2-8}$ alkylenediamines such as N,N'-disalicylideneethylenediamine, N,N'-disalicylidenetrimethylenediamine, and N,N'-disalicylidene-4-aza-1,7-heptanediamine (preferably, N,N'-disalicylidene $C_{2-5}$ alkylenediamine); and N,N'-disalicylidene $C_{6-12}$ arylenediamines such as N,N'-disalicylidene-o-phenylenediamine, and N,N'-disalicylidene-2,2'-biphenylenediamine. Examples of the particularly preferred N,N'-disalicylidenediamine are N,N'-disalicylidene $C_{2-4}$ alkylenediamines such as N,N'-disalicylideneethylenediamine and N,N'-disalicylidenetrimethylenediamine.

As the aromatic rings Z, there may be exemplified hydrocarbon rings (e.g., benzene, naphthalene) and heterocycles (e.g., nitrogen atom-containing heterocycles such as pyridine, pyrazine, pyrimidine, and quinoline; sulfur atom-containing heterocycles such as thiophene; and oxygen atom-containing heterocycles such as furan). As to the substituents $R^1$ and $R^2$ of the aromatic rings Z, examples of the halogen atom are bromine, chlorine, and fluorine atoms, and examples of the alkyl group are $C_{1-6}$ alkyl groups such as methyl, ethyl, propyl, butyl, and t-butyl groups. Examples of the alkoxy group are $C_{1-6}$ alkoxy groups such as methoxy, ethoxy, propoxy, and butoxy groups. Each of the substituents $R^1$ and $R^2$ is usually a hydrogen atom, a $C_{1-4}$ alkyl group, or a hydroxymethyl group.

[Cyclic base]

Any base can be used as the cyclic base provided that it is cyclic and does not adversely affect the oxidative reaction. The cyclic base includes alicyclic or aromatic bases containing at least one (preferably, two) nitrogen atom.

Examples of the alicyclic base include bases in which at least one nitrogen atom constitutes a hetero atom of a ring, for example, 5 to 10-membered mono- and heterocyclic compounds such as pyrrolidine or its derivatives [N-substituted pyrrolidines (e.g., N—$C_{1-4}$ alkylpyrrolidines such as N-methylpyrrolidine), substituted pyrrolidines (e.g., 2- or 3-methylpyrrolidine, 2- or 3-aminopyrrolidine), or the like]; piperidine or its derivatives [N-substituted piperidines (e.g., N—$C_{1-4}$ alkylpiperidine such as N-methylpiperidine; piperylhydrazine), substituted piperidines (o-aminopiperidine, m-aminopiperidine, and p-aminopiperidine)]; alkylene imines or its derivatives [hexamethylene imine, N-substituted hexamethylene imines (e.g., N-methylhexamethylene imine)]; piperazine or its derivatives [N—$C_{1-4}$ alkylpiperazines such as N-methylpiperazine; N,N'-di-$C_{1-4}$ alkylpiperazines such as N,N'-dimethylpiperazine; 2-methylpiperazine]; and poly- and heterocyclic compounds such as azabicyclo $C_{7-12}$ alkanes (e.g., quinuclidine, 1,4-diazabicyclo[2.2.2]octane (DABCO), 1,5-diazabicyclo[3.2.1]octane, 1,5-diazabicyclo [3.3.0]octane, 1,4-diazabicyclo[4.2.0]octane, 1,5-diazabicyclo[3.3.1]nonane, 1,5-diazabicyclo[5.3.0]decane), azatricyclo $C_{8-16}$ alkanes (e.g., 1,5-diazacyclo[3.3.0.0$^{2,6}$] octane, hexamethylenetetramine), and derivatives thereof. Among these alicyclic bases, those containing at least two (particularly, 2 to 6) nitrogen atoms are preferable. The preferred alicyclic base is, for example, 6 to 8-membered mono- and heterocylcic compounds (e.g., piperazine, N-substituted piperazines, amino-substituted piperazines); azabicyclo $C_{7-10}$ alkanes (e.g., quinuclidine, DABCO, or derivatives thereof); and hexamethylenetetramine.

The aromatic base includes those having at least two nitrogen atoms (particularly 2 to 6) and at least one nitrogen atom as a hetero atom is comprised in a ring. Examples of such aromatic bases include a compound having a substituent containing at least a nitrogen atom (e.g., amino group, N-substituted amino groups) on aromatic heterocyclic compounds in which at least one nitrogen atom constitutes a ring (e.g., pyridine), for example, N,N-di-substituted aminopyridines such as 2-, 3-, or 4-aminopyridine, 2-, 3-, or 4-mono- or di-alkylaminopyridines (e.g., di-$C_{1-4}$ alkylaminopyridines such as dimethylaminopyridine), 2-, 3-, or 4-piperidinopyridine, and 4-pyrrolidinopyridine]; pyrazine or derivatives thereof (e.g., 2-methylpyrazine); phthalazine, quinazoline, quinoxaline, or its derivatives; phenanthroline or its derivatives (e.g., 1, 10-phenanthroline); and 2,2-bipyridyl or its derivatives. N,N-di-substituted aminopyridines, pyrazine, phenanthroline, or derivatives thereof are particularly preferred.

In the above cyclic base, another nitrogen atom(s) than the one constituting the ring is preferably a tertiary amine, and the nitrogen atom constituting the ring may be substituted with a substituent other than a hydrogen atom. The cyclic base can be used singly or as a combination of two or more.

The proportion of the cyclic base relative to the complex is about 20/1 to 500/1 (molar ratio) and preferably about 30/1 to 300/1 (e.g., about 50/1 to 250/1).

An oxidation catalytic system according to the present invention may further comprise the above oxidation catalytic system comprising a cyclic base and a complex of a transition metal with an N,N'-disalicylidenediamine, and a basic nitrogen-containing compound. The addition or incorporation of the basic nitrogen-containing compound to the cyclic base and the complex remarkably improves the conversion of β-isophorone and the selectivity of ketoisophorone even when the water content in the reaction system is not controlled at the initial stage of the reaction.

As the nitrogen-containing compound, use can be made of Schiff bases, etc. Examples of the Schiff bases include a compound having, e.g., an imino bond or an anil bond. Such Schiff bases include, for example, compounds shown by the following formulae (2) to (9) and compounds having a similar or analogous structure.

(2)
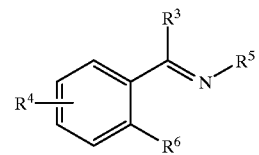

(3)
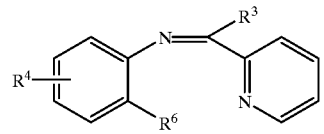

(4)
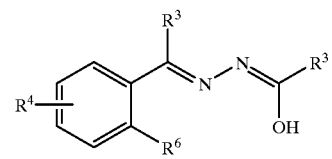

(5)
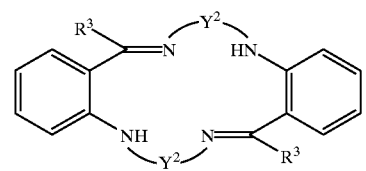

(6)
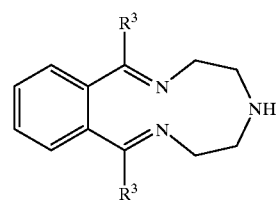

(7)
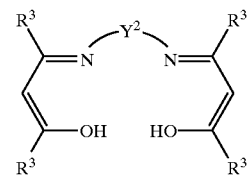

(8)
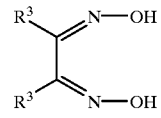

(9)
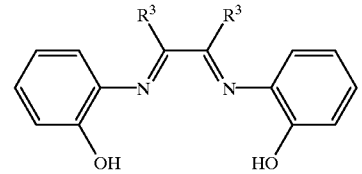

wherein $R^3$ and $R^4$ are the same or different and each represents hydrogen atom, an alkyl group, an aryl group, or a cycloalkyl group; $R^5$ represents ahydroxyl group, an amino group, an alkyl group, or an aryl group; $R^6$ represents a hydroxyl group, an amino group, an alkyl group, an aryl group, or a pyridyl group; and $Y^2$ represents an alkylene group or a cyclohexylene group.

The preferred nitrogen-containing groups includes, for example, salicylaldoxime, bisacetylacetone-ethylenediimine, dimethylglyoxime, diamine salicylaldimines such as N,N'-disalicylideneethylenediamine which constitutes the above-described complex (e.g., N,N'-disalicylidene $C_{2-5}$ alkylenediamines such as N,N'-disalicylidenetrimethylenediamine and N,N'-disalicylidene-4-aza-1,7-heptanediamine), compounds having an imino bond such as bisimine compounds, and compounds having an anil bond such as glyoxal bishydroxyanil. The N,N-disalicylidenediamines constituting the above complex are, for example, a ligand for the complex shown by the formula (1).

The proportion of the basic nitrogen-containing compound relative to the complex is the former/the latter (molar ratio)=about 0.1/1 to 20/1, preferably about 0.5/1 to 15/1 (e.g., 0.5/1 to 10/1), and usually about 1/1 to 10/1.

[Oxidation reaction]

Using the above-described oxidation catalytic system (1) comprising the cyclic base and the complex of the transition metal with the N,N'-disalicylidenediamine, or the oxidation catalytic system (2) comprising the above oxidation catalytic system (1) (i.e., the cyclic base and the complex), and the basic nitrogen-containing compound, β-isophorone or a derivative thereof is oxidized with molecular oxygen to produce a corresponding ketoisophorone or a derivative thereof.

The amount of each constituent of the oxidation catalytic systems (1) and (2) relative to 1 mole of β-isophorone (or a derivative thereof) is as follows.

Complex: about $1 \times 10^{-5}$ to $1 \times 10^{-2}$ mole (preferably, about $1 \times 10^{-4}$ to $1 \times 10^{-3}$)

Cyclic base: about $5 \times 10^{-2}$ to 1 mole (preferably, about $1 \times 10^{-2}$ to 0.5 mole)

Basic nitrogen-containing compound: about $1 \times 10^{-5}$ to $5 \times 10^{-2}$ mole (for example, about $1 \times 10^{-4}$ to $1 \times 10^{-2}$ mole, preferably, about $1 \times 10^{-3}$ to $5 \times 10^{-3}$ mole)

[Substrate]

As a reaction substrate to be oxidized by using the above oxidation catalytic systems, there can be exemplified β-isophorone (3,5,5-trimethylhex-3-ene-1-one) or its derivatives. Further, compounds having a structure similar to that of β-isophorone such as compounds with a 3-cyclohexenone skeleton can also be oxidized to give products similar to ketoisophorone.

[Oxygen source]

In the present invention, in addition to oxygen and oxygen-containing gases, a compound generating molecular oxygen is also employed as an oxygen source so far as capable of providing molecular oxygen. As the oxygen source, highly pure oxygen or a high oxygen content gas may be used, the oxygen gas diluted with an inert gas, e.g., nitrogen, helium, argon, or carbon dioxide is preferably supplied to the reaction system. Moreover, with the oxidation catalytic systems of the present invention, β-isophorone can be oxidized effectively even with air instead of oxygen as the oxygen source. The use of air as the oxygen source is not only highly advantageous in view of economics but also reduces the danger of explosions encountered in industrialization.

The oxygen concentration of the oxygen source is, for example, about 5 to 100% by volume, preferably about 5 to 50% by volume, and particularly about 7 to 30% by volume. Even at such a low oxygen concentration as of about 8 to 25% by volume, the oxidative reaction effectively proceeds.

When supplying molecular oxygen to a reaction vessel or container, the reaction may be carried out in a closed system with enough molecular oxygen previously supplied, or may be conducted in a continuous stream of molecular oxygen. In the case of a stream of molecular oxygen, the flow rate is, for example, about 0.1 to 10 L/min and preferably about 0.5 to 5 L/min per unit volume (1 L) of the vessel.

The oxidative reaction may be either a gas-phase oxidation or a liquid-phase oxidation. The reaction may be carried out in the absence of a solvent or in the presence of a solvent inert to the reaction. Preferably, the reaction is carried out in an inert solvent.

[Reaction solvent]

Any solvent can be used as a reaction solvent so far as it does not impair the oxidative reaction by inactivating the oxidation catalytic system or adversely affect the reaction. In the oxidative reaction using the oxidation catalytic systems of the present invention, water is produced with producing ketoisophorone. Therefore, recovery of the cyclic base can be made easier by appropriately selecting the base, and a water-insoluble organic solvent is particularly preferred from the standpoint of recycling of solvent. Examples of the water-insoluble organic solvent are aliphatic hydrocarbons solvents such as hexane, heptane, and octane; aromatic hydrocarbon such as benzene, toluene, and xylene; alicyclic hydrocarbons such as cyclohexane; ketones (particularly, dialkyl ketones) such as methyl ethyl ketone and dibutyl ketones (e.g., diisobutyl ketone, di-t-butyl ketone); ethers such as diethyl ether, diisopropyl ether, dibutyl ether, tetrahydrofuran, dioxane, ethylene glycol monomethyl ether, ethylene glycol dimethyl ether, diethylene glycol monomethyl ether, and diethylene glycol dimethyl ether; halogen-containing solvents such as monochloroethane, dichloroethane, chloroform, carbon tetrachloride, and 1,2-dichloroethane; and esters such as methyl acetate, ethyl acetate, and butyl acetate. Dialkyl ketones are preferable, and dibutyl ketones are particularly preferred.

When using a solvent, the substrate concentration in the liquid phase of the reaction system is not particularly restricted, and for an effective oxidative reaction, the concentration can be selected from within the range of about 5 to 70% by weight and preferably about 15 to 60% by weight (e.g., 20 to 55% by weight). More preferably, the concentration of the substrate is 22 to 60% by weight (e.g., 25 to 55% by weight, particularly 30 to 55% by weight).

The proportion of the water content in the reaction system at the initial stage of the reaction can be selected from within the range not adversely affecting the reaction such as inactivation of the catalytic system, and is about 1% by weight or less (about 0.001 to 1% by weight) and preferably about 0.5% by weight or less (about 0.001 to 0.5% by weight). Despite acceleration of the reactionat the initial stage, water content exceeding 1% by weight results in a subsequent cessation of the reaction or a decrease in the selectivity of ketoisophorone. The water in the reaction system includes not only the water contained at the beginning or initial stage of the reaction but also the water produced by the reaction. In the present reaction system, there is usually present a finite amount of water. In the present invention, usually, water is not added to the reaction system. It is desirable that the water produced by the reaction is removed from the system. The amount of the produced water varies with the concentration of β-isophorone substrate, and the amount of the water to be removed is at least about 30% by weight, preferably at least about 50% by weight, and more preferably at least about 80% by weight, relative to the total amount of the water produced.

The reaction temperature can be selected according to the reaction rate, selectivity, and a solvent to be used. To eliminate the risk of explosions, it is desirable that the reaction is conducted at a temperature lower than the flash point of the reaction solvent. For example, in the case of diisobutyl ketone (flash point: about 49° C.) employed as the solvent, the reaction is preferably carried out at a temperature within the range of about 35 to 45° C. Moreover, the reaction can be conducted either at atmospheric pressure or under applied pressure [to about 150 atm ($152\times10^5$ Pa)] but preferably at atmospheric pressure. The reaction time (residence time in a flow reaction) is not particularly restricted, and usually about 0.5 to 30 hours (e.g., 1 to 10 hours). The reaction can be carried out in a conventional system such as a batch system, a semi-batch system, or a continuous system. In the continuous system, part of a catalyst component or the catalytic system is continuously or intermittently removed from a reactor for regeneration, and the regenerated catalyst may be recycled to the reactor to be reused. In the batch system, a catalyst component or the catalytic system may be separated and recovered from a reaction product after completion of the reaction, wholly or partially regenerated and may be reused repeatedly as a catalyst component or a catalytic system for the reaction.

By oxidizing β-isophorone or a derivative thereof with molecular oxygen in the presence of the oxidation catalytic systems comprising the above complex, the cyclic base and, if needed, the basic nitrogen-containing compound, the corresponding 4-oxoisophorone (ketoishophorone) or a derivative thereof can be produced.

Ketoisophorone produced by the reaction can easily be separated and purified with a conventional separation technique such as filtration, condensation, distillation, extraction, crystallization, recrystallization and column chromatography, or a combination thereof. Particularly, according to the present invention, the conversion of β-isophorone and the selectivity of ketoisophorone can be significantly improved, and the production of by-product(s) is remarkably inhibited. Therefore, even though the separation and purification step is required of ketoisophorone, ketoisophorone can be separated and purified with easiness and efficiency, and therefore need not be highly separation-purified.

According to the present invention, with an oxidation catalytic system comprising the cyclic base and the complex of the transition metal with an N,N'-disalycylidenediamine, ketoisophorone or a derivative thereof can be produced by oxidizing β-isophorone or a derivative thereof with molecular oxygen without adding an organic acid having a pKa value of 2 to 7 or the corresponding aldehyde, a $C_{1-4}$ aliphatic alcohol or a phenol, a compound capable of forming the enolic form, or lithium sulfate. Further, the production of by-product(s) is significantly inhibited, and ketoisophorone or a derivative thereof is produced with high conversion and high selectivity.

EXAMPLES

The following examples are intended to show the present invention in further detail and should be no means be construed as defining the scope of the invention.

The substrate, complex (transition metal complex), bases, nitrogen-containing compounds, and the solvent used in Examples and Comparative Examples are as follows.

1. Substrate (a-1): β-isophorone

2. Transition metal complex (b-1): Manganese-salen complex

A manganese complex was obtained in accordance with a method recited in the J. Am. Chem. Soc., 108 (1986) 2317. To be exact, a solution of 0.90 g (16 mmol) of potassium hydroxide and 20 ml of methanol was added to a mixed solution of 2.15 g (8 mmol) of N,N'-disalicylideneethylenediamine (EDSA) and 50 ml of methanol, and to the resultant mixture was added a solution of 1.98 g (8.08 mmol) of manganese acetate·tetrahydrate Mn $(OAc)_2 \cdot 4H_2O$ and 30 ml of methanol in a nitrogen stream, followed by stirring at a reflux temperature for 5 hours. Thereafter, the reaction mixture was cooled to room temperatures taking 2 hours and then filtered. The cake or residue was washed with 10 ml of methanol, and filtered, and dried in vacuo at 100° C. for 8 hours. Thus, there is obtained a manganese complex.

Thermal analysis (TC/TDA) of the manganese complex showed no clear endoergic peak and revealed the complex to be noncrystalline (amorphous). The melting point of the sole EDSA was 127.6° C.

Elemental analysis Found: C, 59.6; H, 4.3; N, 8.7. Calculated: C, 59.8; H, 4.4; N, 8.7.

3. Base (c-1): 1,4-diazabicyclo[2.2.2]octane (DABCO)

(c-2): 4-dimethylaminopyridine (c-3): 2-dimethylaminopyridine (c-4): 1,10-phenanthroline (c-5): 1,3,6,8,10,13,16,19-octazabicyclo[6,6,6]eicosane (d-1): triethylamine (d-2): dimethylaniline 4. Nitrogen-containing compound (e-1): salicylaldoxime (e-2): dimethylglyoxime (e-3): bisacetylacetone-ethylenediimine (e-4): N,N'-disalicylideneethylenediamine ($H_2$salen)

5. Solvent (f-1): diisobutyl ketone

Examples 1 to 8 and Comparative Examples 1 to 5

A glass reactor (capacity: 1 L) equipped with a mechanical stirrer with turbine blades and a molecular oxygen gas inlet tube having a porous glass unit was fed with β-isophorone, manganese-salen complex, base, and solvent in amounts shown in Table 1, and the reaction was carried out with flowing air or oxygen gas at a constant flow rate.

For comparison, the same reaction was conducted also for the case with a non-cyclic base as the base, the case with an aromatic base having no nitrogen atom as a hetero atom of the aromatic ring as the base, and the case in which water was added at the beginning or initial stage of the reaction.

The conversions of β-isophorone and the selectivities of from β-isophorone to ketoisophorone in Examples 1 to 8 and Comparative Examples 1 to 5 are shown in Table 1 with the reaction conditions.

TABLE 1

| | β-IP (g) (weight %) | Mn-salen (g) (ppm) | Base (g) | Amount of water added at the beginning of the reaction (weight %) | Solvent (g) | Air flow rate (L/min) (oxygen concentration volume %) | Reaction temperature (° C.) | Reaction Time (hr) | Conversion (%) | Selectivity (%) |
|---|---|---|---|---|---|---|---|---|---|---|
| Example 1 | 133 (23.7) | 0.24 427 | c-1 8.5 | 0 | 420 | 1.4 (21) | 40 | 4 | 89 | 90 |
| Example 2 | 250 (43.1) | 0.32 551 | c-1 10.0 | 0 | 320 | 1.8 (21) | 40 | 4 | 92 | 89 |
| Example 3 | 300 (53.6) | 0.36 642 | c-1 10.0 | 0 | 250 | 2 (21) | 40 | 4 | 92 | 84 |
| Example 4 | 200 (34.4) | 0.28 481 | c-1 12.0 | 0 | 370 | 2.5 (10) | 40 | 5 | 94 | 90 |
| Example 5 | 133 (23.7) | 0.32 570 | c-1 8.5 | 0 | 420 | 1.2 (21) | 40 | 5 | 93 | 89 |
| Example 6 | 250 (42.9) | 0.32 549 | c-2 12.2 | 0 | 320 | 1.8 (21) | 40 | 4 | 90 | 88 |
| Example 7 | 200 (34.4) | 0.28 481 | c-3 12.2 | 0 | 370 | 1.7 (21) | 40 | 4 | 88 | 90 |
| Example 8 | 250 (43.1) | 0.32 552 | c-4 9.5 | 0 | 320 | 1.5 (21) | 35 | 5 | 90 | 88 |
| Comp. Ex. 1 | 200 (35.8) | 0.24 430 | d-1 18.0 | 0 | 340 | 1.4 (21) | 40 | 4 | 21 | 75 |
| Comp. Ex. 2 | 200 (35.8) | 0.24 430 | d-1 18.0 | 0 | 340 | 0.8 (100) | 40 | 4 | 88 | 68 |
| Comp. Ex. 3 | 200 (35.3) | 0.24 423 | d-2 35.0 | 0 | 332 | 1.4 (21) | 40 | 4 | 2 | — |
| Comp. Ex. 4 | 133 (23.7) | 0.24 427 | c-1 8.5 | 1.2 | 420 | 1.4 (21) | 40 | 4 | 88 | 83 |
| Comp. Ex. 5 | 133 (23.7) | 0.24 427 | c-1 8.5 | 5.0 | 420 | 1.4 (21) | 40 | 4 | 85 | 65 |

Examples 9 to 15

A glass reactor (capacity: 1 L) equipped with a mechanical stirrer with turbine blades and a molecular oxygen gas inlet tube having a porous glass unit was fed with β-isophorone, manganese-salen complex, base, nitrogen-containing compound, and solvent in amounts shown in Table 2. The reaction was conducted with air flowing at a constant flow rate.

The conversions of β-isophorone and the selectivities of from β-isophorone to ketoisophorone are shown in Table 2 with the reaction conditions.

in Comparative Examples. In Examples, the conversions and selectivities were improved as compared with those with the reaction systems to which water was added so that the water content at the initial stage of the reaction exceeded 1% by weight (Comparative Examples 5 and 6). Moreover, in the cases of a catalytic system to which a nitrogen-containing compound was added (Examples 9 to 15), the conversions and selectivities were more improved than those in Examples 1 to 8.

What is claimed is:

1. An oxidation catalytic system for producing ketoisophorone or a derivative thereof by oxidizing β-isophorone or

TABLE 2

| | β-IP (g) (weight %) | Mn-salen (g) (ppm) | Base (g) | Nitrogen-containing compound (g) | Solvent (g) | Air flow rate (L/min) (oxygen concentration volume %) | Reaction temperature (° C.) | Reaction Time (hr) | Conversion (%) | Selectivity (%) |
|---|---|---|---|---|---|---|---|---|---|---|
| Example 9 | 133 (23.7) | 0.24 (427) | c-1 8.5 | e-1 0.14 | 420 | 1.4 (21) | 40 | 4 | 96 | 91 |
| Example 10 | 250 (43.1) | 0.32 (551) | c-1 10.0 | e-2 0.18 | 320 | 1.8 (21) | 40 | 4 | 95 | 85 |
| Example 11 | 200 (34.4) | 0.28 (481) | c-1 12.2 | e-3 0.31 | 370 | 1.7 (21) | 40 | 4 | 98 | 90 |
| Example 12 | 250 (43.1) | 0.32 (551) | c-1 10.0 | e-4 0.40 | 320 | 1.8 (21) | 40 | 4 | 96 | 88 |
| Example 13 | 300 (53.6) | 0.36 (642) | c-1 10.0 | e-4 0.53 | 250 | 2 (21) | 45 | 4 | 99 | 85 |
| Example 14 | 200 (34.4) | 0.28 (481) | c-1 12.0 | e-4 0.52 | 370 | 2.5 (10) | 40 | 5 | 99 | 91 |
| Example 15 | 133 (23.7) | 0.24 (427) | c-5 5.0 | e-4 0.50 | 420 | 1.4 (21) | 40 | 4 | 96 | 92 |

As obvious from Tables 1 and 2, in Examples in which a cyclic base was used as the base, the conversions and selectivities were highly improved as compared with those a derivative thereof with molecular oxygen with controlling a water content in a reaction system to 1% by weight or less at the initial stage of the reaction, which comprises a cyclic base and a complex of a transition metal with an N,N'-disalicylidenediamine, wherein the system is without the addition of (i) an organic acid having a pKa value of 2 to 7 or an aldehyde of the organic acid, (ii) a compound which can form an enol structure, and (iii) lithium sulfate.

2. A process for producing ketoisophorone or derivatives thereof, which comprises oxidizing β-isophorone or a derivative thereof with molecular oxygen in the presence of a catalytic system comprising a cyclic base and a complex of a transition metal with an N,N'-disalicylidenediamine with controlling a water content in a reaction system to 1% by weight or less at the initial stage of the reaction, wherein the system is without the addition of (i) an organic acid having a pKa value of 2 to 7 or an aldehyde of the organic acid, (ii) a compound which can form an enol structure, and (iii) lithium sulfate.

3. A process according to claim 2, wherein the content of β-isophorone or a derivative thereof in the reaction system is 22 to 60% by weight and the oxidation is conducted with the water content of 1% by weight or less at the initial stage without adding water.

4. A process according to claim 2, wherein the water content is controlled to 0.5% by weight or less.

5. An oxidation catalytic system for producing ketoisophorone or a derivative thereof by oxidizing β-isophorone or a derivative thereof with molecular oxygen, which comprises a complex of a transition metal with an N,N'-disalicylidenediamine, a cyclic base, and a basic nitrogen-containing compound, wherein the system is without the addition of (i) an organic acid having a pKa value of 2 to 7 or an aldehyde of the organic acid, (ii) a compound which can form an enol structure, and (iii) lithium sulfate.

6. An oxidation catalytic system according to claim 5, wherein said transition metal is an element selected from the group consisting of the Groups 5, 7, 8, 9, and 11 of Periodic Table of the Elements.

7. An oxidation catalytic system according to claim 5, wherein said N,N'-disalicylidenediamine is at least one member selected from the group consisting of N,N'-disalicylidene $C_{2-8}$ alkylenediamines and N,N'-disalicylidene $C_{6-12}$ arylenediamines.

8. An oxidation catalytic system according to claim 5, wherein said complex is a complex of at least one transition metal selected from the group consisting of manganese, iron, cobalt, copper and vanadium with an N,N'-disalicylidene $C_{2-5}$ alkylenediamine.

9. An oxidation catalytic system according to claim 5, wherein said cyclic base is an alicyclic or aromatic base having at least one nitrogen atom as a hetero atom.

10. An oxidation catalytic system according to claim 5, wherein said cyclic base is at least one member selected from the group consisting of 5 to 10-membered mono- and heterocyclic compounds, azabicyclo $C_{7-12}$ alkanes, azatricyclo $C_{8-16}$ alkanes, and aromatic heterocyclic compounds containing at least one nitrogen atom as a hetero atom and having an amino group or an N-substituted amino group or both.

11. An oxidation catalytic system according to claim 5, wherein the proportion of said cyclic base to said complex is 20/1 to 500/1 (molar ratio).

12. An oxidation catalytic system according to claim 5, wherein said basic nitrogen-containing compound is a Schiff base.

13. An oxidation catalytic system according to claim 5, wherein said basic nitrogen-containing compound is a compound selected from the group consisting of imino compounds and anil compounds.

14. An oxidation catalytic system according to claim 5, wherein said basic nitrogen-containing compound is a compound shown by the following formulae (2) to (9):

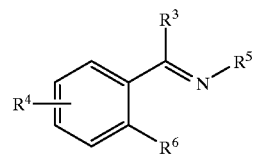

(2)

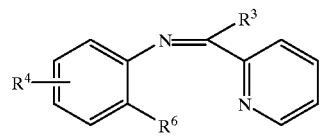

(3)

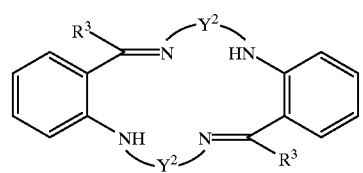

(4)

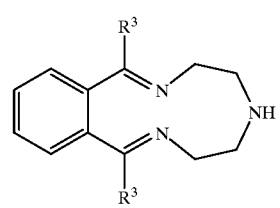

(5)

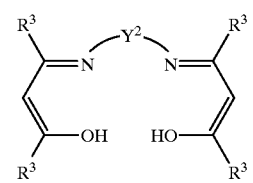

(6)

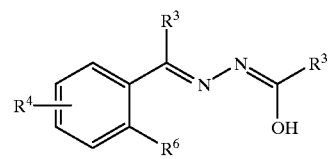

(7)

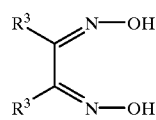

(8)

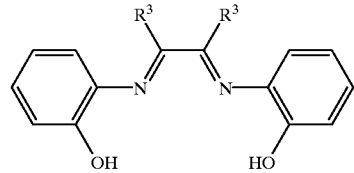

(9)

wherein $R^3$ and $R^4$ are the same or different and each represents hydrogen atom, an alkyl group, an aryl group, or a cycloalkyl group; $R^5$ represents a hydroxyl group, an amino group, an alkyl group, or an aryl group; $R^6$ represents a hydroxyl group, an amino group, an alkyl group, an aryl group, or a pyridyl group; and $Y^2$ represents an alkylene group or a cyclohexylene group.

15. An oxidation catalytic system according to claim 5, wherein the proportion of said basic nitrogen-containing compound to said complex is 0.1/1 to 20/1 (molar ratio).

16. An oxidation catalytic system according to claim 5, which comprises (1) a complex of manganese with an N,N'-disalicylidene $C_{2-4}$ alkylenediamine, (2) a cyclic base having 2 to 6 nitrogen atoms in which at least one nitrogen atom constitutes a hetero atom of a ring, and (3) a basic nitrogen-containing compound comprising a Schiff base having an imino group or an amino group or both, and the proportion of the cyclic base to the complex is 30/1 to 300/1 (molar ratio) and the proportion of the basic nitrogen-containing compound to the complex is 0.5/1 to 15/1 (molar ratio).

17. A process for producing ketoisophorone or a derivative thereof, which comprises oxidizing β-isophorone or a derivative thereof with molecular oxygen using an oxidation catalytic system recited in claim 5 to produce a ketoisophorone or a derivative thereof.

18. A process according to claim 17, wherein said oxidation catalytic system comprises $1\times10^{-5}$ to $1\times10^{-2}$ mole of a complex, $5\times10^{-2}$ to 1 mole of a cyclic base, and $1\times10^{-5}$ to $5\times10^{-2}$ mole of a basic nitrogen-containing compound, relative to 1 mole of said β-isophorone or a derivative thereof.

19. A process according to claim 17, wherein said oxidation is conducted in a ketone-series solvent.

* * * * *